US007008624B1

(12) United States Patent
Grabstein et al.

(10) Patent No.: US 7,008,624 B1
(45) Date of Patent: Mar. 7, 2006

(54) ANTAGONISTS OF INTERLEUKIN-15

(75) Inventors: Kenneth H. Grabstein, Mercer Island, WA (US); Dean K. Pettit, Seattle, WA (US); Raymond J. Paxton, Bellevue, WA (US)

(73) Assignee: Immunex Corporation, Thousand Oaks, CA (US)

( * ) Notice: Subject to any disclaimer, the term of this patent is extended or adjusted under 35 U.S.C. 154(b) by 0 days.

(21) Appl. No.: 09/578,669

(22) Filed: May 25, 2000

Related U.S. Application Data

(60) Continuation of application No. 09/196,427, filed on Nov. 20, 1998, now Pat. No. 6,177,079, which is a continuation of application No. 09/134,456, filed on Aug. 14, 1998, now Pat. No. 6,168,783, which is a division of application No. 08/392,317, filed on Feb. 22, 1995, now Pat. No. 5,795,966.

(51) Int. Cl.
*A61K 39/00* (2006.01)
*A61K 39/38* (2006.01)
*A61K 39/385* (2006.01)
*C12P 21/06* (2006.01)
*C07K 1/00* (2006.01)

(52) U.S. Cl. ............................... 424/184.1; 424/185.1; 424/193.1; 435/68.1; 514/2; 530/350; 530/351; 530/354; 530/362; 530/380

(58) Field of Classification Search ................ 530/350, 530/354, 362, 380, 351; 424/184.1, 185.1, 424/193.1, 68.1; 514/2
See application file for complete search history.

(56) References Cited

U.S. PATENT DOCUMENTS

| 4,853,332 | A |   | 8/1989  | Mark et al.        |
| 5,206,344 | A |   | 4/1993  | Katre et al.       |
| 5,208,020 | A |   | 5/1993  | Chari et al.       |
| 5,440,021 | A |   | 8/1995  | Chuntharapai et al.|
| 5,539,063 | A | * | 7/1996  | Hakimi et al.      |
| 5,552,303 | A |   | 9/1996  | Grabstein et al.   |
| 5,574,138 | A |   | 11/1996 | Grabstein et al.   |
| 5,696,234 | A |   | 12/1997 | Zurawski et al.    |
| 5,707,616 | A |   | 1/1998  | Grabstein et al.   |
| 5,747,024 | A |   | 5/1998  | Grabstein et al.   |
| 5,892,001 | A |   | 4/1999  | Grabstein et al.   |

FOREIGN PATENT DOCUMENTS

WO    WO 96/04306    2/1996

OTHER PUBLICATIONS

Grabstein, K. et al., "Cloning of a T Cell Growth Factor That Interacts with the β Chain of the Interleukin-2 Receptor", *Science* 264:965-968, 1994.
McMahan, C. et al., "A novel IL-1 receptor, cloned from B cells by mammalian expression, is expressed in many cell types," *The EMBO Journal* 10(10):2821-2832.
Giri, J. et al., "Utilization of the β and γ chains of the IL-2 receptor by the novel cytokine IL-15," *The EMBO Journal* 13:2822-2830, 1994.
Carson, W. et al., "Interleukin (IL) 15 is a Novel Cytokine that Activates Human Natural Killer Cells via Components of the IL-2 Receptor," *Journal Exp. Medicine* 180: 1395-1403, 1994.
Armitage, R. et al., "IL-15 Has Stimulatory Activity for the Induction of B Cell Proliferation and Differentiation," *The Journal of Immunology* 154: 483-489, 1995.
Tinubu, S. et al., "Humanized Antibody Directed to the IL-2 Receptor β-Chain Prolongs Primate Cardiac Allograft Survival," *The Journal of Immunology:* 153:4330-4338. 1994.
Sevier, E.D. et al., "Monoclonal Antibodies in Clinical Immunology," *Clinical Chemistry* 27 :1797-1806, 1981.
Collins, L., et al., "Identification of specific residues of human interleukin 2 that affect binding to the 70-kDa subunit (p70) of the interleukin 2 receptor," *Proc. Natl. Acad. Sci. USA* 85: 7709-7713, 1988.
Ju, G., et al., "Structure-Function Analysis of Human Interleukin-2," *J. Biol. Chem.* 262: 5723-5731, 1987.
Zurawski, S., et al., "Definition and spatial location of mouse interleukin-2 residues that interact with its heterotrimeric receptor," *EMBO J.* 12(13): 5113-5119, 1993.
Harlow et al. "Antibodies: A Laboratory Manual," published by *Cold Spring Harbor Laboratories*, 285-287.
Harris et al., "Therapeutic antibodies—the coming of age," *Tibtech* 11:12-44, 1993.
Ferrara et al., "Amelioration of Acute Graft VS Host Disease Due to Minor Histocompatibility Antigens by In Vivo Administration of Anti-Interleukin 2 Receptor Antibody," *The Journal of Immunology,* 137(6):1874-1877, 1986.

* cited by examiner

*Primary Examiner*—Mark Navarro
(74) *Attorney, Agent, or Firm*—Jane E. R. Potter; Davis Wright Tremaine LLP

(57) ABSTRACT

Antagonists of mammalian interleukin-15 ("IL-15") are disclosed and include muteins of IL-15 and modified IL-15 molecules that are each capable of binding to the IL-15Rα-subunit and that are incapable of transducing a signal through either the β- or γ-subunits of the IL-15 receptor complex. Also included are monoclonal antibodies against IL-15 that prevent IL-15 from effecting signal transduction through either the β- or γ-subunits of the IL-15 receptor complex. Methods of treating various disease states are disclosed, including treating allograft rejection and graft-versus-host disease.

38 Claims, No Drawings

ANTAGONISTS OF INTERLEUKIN-15

This is a Continuation of application Ser. No. 09/196,427, filed Nov. 20, 1998, now U.S. Pat. No. 6,177,079, which is a Continuation of application Ser. No. 09/134,456, filed Aug. 14, 1998, now U.S. Pat. No. 6,168,783, which is a Divisional of application Ser. No. 08/392,317, filed Feb. 22, 1995, now U.S. Pat. No. 5,795,966.

FIELD OF THE INVENTION

The present invention relates generally to antagonists of a mammalian epithelium-derived T-cell factor polypeptide referred to herein as interleukin-15 ("IL-15"). It more particularly relates to muteins of IL-15, monoclonal antibodies against IL-15 and IL-15 conjugates that each significantly reduce the ability of IL-15 to stimulate the proliferation of T-lymphocytes in an in vitro CTLL assay. Also included in the invention are methods for treating various disease states in mammals where a reduction in IL-15 activity is desired.

BACKGROUND OF THE INVENTION

Interleukin-15 is a known T-cell growth factor that can support proliferation of an IL-2-dependent cell line, CTLL-2. IL-15 was first reported by Grabstein et al., in *Science*, 264:965 (1994) as a secreted cytokine comprising a 162-amino acid precursor polypeptide that contains a 48-amino acid leader sequence that results in a 114-amino acid mature protein. Grabstein et al. also describe the cloning of the full-length human cDNA encoding the 162-amino acid precursor, which contains a 316 bp 5' noncoding region and a 486 bp open reading frame (or a 489 bp open reading frame when including the 3 bp for the stop codon) and a 400 bp 3' noncoding region.

IL-15 shares many properties with IL-2. These properties include proliferation and activation of human and murine T cells, the induction of lymphokine activated killer cell (LAK) activity, natural killer cell (NK) activity, and cytotoxic T lymphocytes (CTL) activity, and costimulation of B cell proliferation and differentiation.

Additionally, IL-15 and IL-2 are structurally homologous molecules that are able to bind to at least three distinct receptor subunits on the T cell membrane surface. IL-2 receptors contain at least three subunits, α, β and γ (Toshikazu et al., *Science*, 257:379 (1992)). Both IL-15 and IL-2 share binding to a common β- γ subunit complex, while each of IL-15 and IL2 bind to a specific α-receptor subunit (IL-15Rα and IL-2Rα, respectively). Recently, the IL-15Rα was discovered and is the subject of copending application Ser. No. 08/300,903, now U.S. Pat. No. 5,591,630. Antibodies directed against the α-chain of the IL-2 receptor (anti-IL-2Rα) have no effect on IL15 binding (Grabstein et al., Id.). Antibodies directed against the β-subunit of the IL-2 receptor, i.e., TU27, TU11, or Mikβ1, however, are able to block the activity of IL-15, suggesting that IL-15 uses the β-subunit for signaling. Similarly, the γ-chain of the IL-2 receptor is required for signal transduction (Giri et al., *EMBO J.*, 13:2822 (1994)). The combination of the β and the γ-subunits of the IL-15 receptor complex, but neither subunit alone, bound IL-15 on transfected COS cells.

Certain disease states and physiological conditions are mediated by T cells. Such diseases include organ transplant rejection, graft versus host disease, autoimmune disease, rheumatoid arthritis, inflammatory bowel disease, dermatologic disorders, insulin-dependent diabetes mellitus, ocular disorders and idiopathic nephrotic syndrome/idiopathic membranous nephropathy. Indeed, allograft rejection and graft-versus-host disease (GVHD) have been associated with increased IL-2 receptor expression. T cells activated in response to foreign histocompatibility antigens appear to express the IL-2 receptor complex. Various therapies have been proposed and studied. For example, Tinubu et al. (*J. Immunol.*, 153:4330 (1994)), reported that the anti-IL-2Rβ monoclonal antibody, Mikβ1, prolongs primate cardiac allograft survival. There is an increase in IL-2Rβ-subunit expression on CD4- and CD8-expressing cells in association with acute allograft rejection, which indicates that the IL-2Rβ-subunit expression seems to increase on alloreactive T cells. See, for example, Niguma et al., *Transplantation*, 52:296 (1991).

However, prior to the present invention, there have been no therapies that focused on the IL-15 ligand-receptor interaction as a means of treating GVHD or in promoting allograft survival.

SUMMARY OF THE INVENTION

The invention is directed to IL-15 antagonists and a method of using the antagonists for treatment of human disease. In particular, such treatment includes promoting allograft survival in mammals and treating GVHD. The IL-15 antagonists are effective by preventing IL-15 from transducing a signal to a cell through either the β- or γ-subunits of the IL-15 receptor complex, thereby antagonizing IL-15's biological activity. Certain of the antagonists according to the invention may interfere with the binding of IL-15 to the β- or γ-subunits of the IL-15 receptor complex, while not substantially interfering with the binding of IL-15 to IL-15Rα.

Antagonists according to the invention include muteins of mature, or native, IL-15, wherein IL-15 has been mutagenized at one or more amino acid residues or regions that play a role in binding to the β- or γ-subunit of the IL-15 receptor complex. Such muteins prevent IL15 from transducing a signal to the cells through either of the β- or γ-subunits of the IL-15 receptor complex, while maintaining the high affinity of IL-15 for the IL-15Rα. Typically, such muteins are created by additions, deletions or substitutions at key positions, for example, $Asp^{56}$ or $Gln^{156}$ of simian and human IL-15 as shown in SEQ ID NOS: 1 and 2, respectively. It is believed that the $Asp^{56}$ affects binding with the β-subunit and that the $Gln^{156}$ affects binding with the γ-subunit of the IL-15 receptor complex.

In addition, the invention encompasses monoclonal antibodies that immunoreact with mature IL-15 and prevent signal transduction to the IL-15 receptor complex.

Further included in the scope of the invention are modified IL-15 molecules that retain the ability to bind to the IL-15Rα, but have substantially diminished or no affinity for the β- and/or γ-subunits of the IL-15 receptor complex. Modified IL-15 molecules can take any form as long as the modifications are made in such a manner as to interfere with or prevent binding, usually by modification at or near the target binding site. Examples of such modified IL-15 molecules include mature IL-15 or a mutein of IL-15 that is covalently conjugated to one or more chemical groups that sterically interfere with the IL-15/IL-15 receptor binding. For example, mature IL-15 may contain site-specific glycosylation or may be covalently bound to groups such as polyethylene glycol (PEG), monomethoxyPEG (mPEG), dextran, polyvinylpyrrolidone (PVP), polyvinyl alcohol (PVA), poly amino acids such as poly-L-lysine or polyhistidine, albumin, gelatin at specific sites on the IL-15 molecule that can interfere with binding of IL-15 to the β- or γ-chains of the IL-15 receptor complex, while maintaining the high affinity of IL-15 for the IL-15Rα. By taking advantage of the steric hindrance properties of the group, binding to specific receptor subunits can be antagonized. Other advantages of conjugating chains of PEG to proteins such as IL-2, GM-CSF, asparaginase, immunoglobulins, hemoglobin, and others are known in the art. For example, it is known that PEG prolongs circulation half-lives in vivo (see, Delgado, et al., *Crit. Rev. Ther. Drug Carr. Syst.*, 9:249 (1992)), enhances solubility (see, Katre, et al., *Proc. Natl. Acad. Sci.*, 84:1487 (1987)) and reduces immunogenicity (see, Katre, N. V., *Immunol.* 144:209 (1990)).

The invention also is directed to the use of the antagonists in a method of treating a disease or condition in which a reduction in IL-15 activity on T cells is desired. Such diseases include organ transplant rejection, graft versus host disease, autoimmune disease, rheumatoid arthritis, inflammatory bowel disease, dermatologic disorders, insulin-dependent diabetes mellitus, ocular disorders and idiopathic nephrotic syndrome/idiopathic membranous nephropathy. In particular, in allograft rejection, IL-15 activity may lead to a host immune response against the graft and eventually rejection. Similarly, in GVHD, the graft, typically a bone marrow transplant, imparts an immune response against the host. Suppression of such activities by the IL-15 antagonists according to the invention may be advantageous in promoting and prolonging graft survival, and in treating GVHD.

Various investigators have reported the prolongation of graft survival by using antibodies, such as anti-TAC, an anti-human IL-2 α-receptor monoclonal antibody. See Reed et al., *Transplantation*, 47:55–59 (1989), wherein anti-TAC is shown to have improved primate renal allograft transplantation. Also, Brown et al., *Proc. Natl. Acad. Sci.*, 88:2663 (1991) describe the use of humanized anti-TAC in prolonging primate cardiac allograft survival. Kirkman et al., *Transplantation*, 51:107 (1991), also describe a clinical trial involving anti-TAC in preventing early allograft rejection. Since IL-15 possesses many biological activities similar to IL-2, and indeed, shares certain receptor subunits with IL-2, interfering with a deleterious activity of IL-15 in diseased conditions has distinct therapeutic potential.

DETAILED DESCRIPTION OF THE INVENTION

The invention is directed to an antagonist of IL-15 activity that interferes with the signal transduction of IL-15 through its receptor complex. In particular, the IL-15 antagonists of the invention are selected from the group consisting of (a) a mutein of mature, or native, IL-15 capable of binding to the α-subunit of the IL-15 receptor and incapable of transducing a signal through the β- and/or γ-subunits of the IL-15 receptor complex; (b) a monoclonal antibody against IL-15 that prevents IL-15 from effecting signal transduction through the β- and/or γ-subunits of the IL-15 receptor complex; and (c) an IL-15 molecule that is covalently bonded with a chemical group that interferes with the ability of IL-15 to effect a signal transduction through either the β- or γ-subunits of the IL-15 receptor complex, but does not interfere with IL-15 binding to IL-15Rα. Also included in the scope of the present invention are the DNAs that encode the muteins described above.

As used herein, "Recombinant DNA technology" or "recombinant" refers to techniques and processes for producing specific polypeptides from microbial (e.g., bacterial, insect or yeast) or mammalian cells or organisms (e.g., transgenics) that have been transformed or transfected with cloned or synthetic DNA sequences to enable biosynthesis of heterologous peptides. Native glycosylation patterns will only be achieved with mammalian cell expression systems. Yeast provide a distinctive glycosylation pattern. Prokaryotic cell expression (e.g., *E. coli*) will generally produce polypeptides without glycosylation.

A "nucleotide sequence" refers to a polynucleotide in the form of a separate fragment or as a component of a larger DNA construct, that has been derived from DNA or RNA isolated at least once in substantially pure form (i.e., free of contaminating endogenous materials) and in a quantity or concentration enabling identification, manipulation, and recovery of its component nucleotide sequences by standard biochemical methods (such as those outlined in Sambrook et al., *Molecular Cloning: A Laboratory Manual*, 2nd ed., Cold Spring Harbor Laboratory, Cold Spring Harbor, N.Y. (1989)). Such sequences are preferably provided in the form of an open reading frame uninterrupted by internal nontranslated sequences, or introns, that are typically present in eukaryotic genes. Sequences of non-translated DNA may be present 5' or 3' from an open reading frame, where the same do not interfere with manipulation or expression of the coding regions.

"Recombinant expression vector" refers to a plasmid comprising a transcriptional unit comprising an assembly of (1) a genetic element or elements having a regulatory role in gene expression, for example, promoters or enhancers, (2) a structural or coding sequence that encodes IL-15 or an IL-15 mutein, and (3) appropriate transcription and translation initiation sequences and, if desired, termination sequences. The representative examples of various regulatory elements that can be used are discussed below (see Recombinant DNA Techniques). Structural elements intended for use in yeast expression systems preferably include a leader sequence enabling extracellular secretion of translated polypeptide by a yeast host cell. Alternatively, in a bacterial expression system, the recombinant polypeptide may include a N-terminal methionine residue. The N-terminal methionine residue may be subsequently cleaved from the expressed recombinant polypeptide to provide a product suitable for further purification.

"Recombinant microbial expression system" refers to a substantially homogeneous monoculture of suitable host microorganisms, for example, bacteria, such as *E. coli*, or yeast, such as *S. cerevisiae*, that have stably integrated a recombinant transcriptional unit into chromosomal DNA or carry the recombinant transcriptional unit as a component of a resident plasmid. Generally, host cells constituting a recombinant microbial expression system are the progeny of a single ancestral transformed cell. Recombinant microbial expression systems will express heterologous polypeptides upon induction of the regulatory elements linked to a structural nucleotide sequence to be expressed.

"IL-15 mutein" or "muteins of IL-15" refer to the mature, or native, simian IL-15 molecules having the sequence of amino acids 49–162 of SEQ ID NO:1 or human IL-15 molecules having the sequence of amino acids 49–162 of SEQ ID NO:2, that have been mutated in accordance with the invention in order to produce an antagonist of IL-15. Such IL-15 muteins are capable of binding to the IL-15Rα subunit, and are incapable of transducing a signal through the β- or γ-subunits of the IL-15 receptor complex.

Preparation of IL-15

Human or simian IL-15 can be obtained according to the procedures described by Grabstein et al., *Science*, 264:965

(1994), which has been incorporated herein by reference, or by conventional procedures such as polymerase chain reaction (PCR). A deposit of human IL15 cDNA was made with the American Type Culture Collection, Rockville, Md., USA (ATCC) on Feb. 19, 1993 and assigned accession number 69245. The deposit was named "I41-hETF." The deposit was made according to the terms of the Budapest Treaty.

IL-15 Muteins

There are many possible mutations of IL-15 that can produce antagonists. Such mutations can be made at specific amino acid sites believed to be responsible for β- or γ-subunit signaling; or mutations can be made over entire regions of IL-15 that are considered necessary for β- or γ-subunit signaling. Typically, mutations may be made as additions, substitutions or deletions of amino acid residues. Preferably, substitution and deletion muteins are preferred with substitution muteins being most preferred.

It is believed that the $Asp^{56}$ affects binding with the β-subunit and that the $Gln^{156}$ affects binding with the γ-subunit of the IL-15 receptor complex. Adding or substituting other naturally-occurring amino acid residues near or at sites $Asp^{56}$ and $Gln^{156}$ can affect the binding of IL-15 to either or both of the β- or γ-subunits of the IL-15 receptor complex. Indeed, removing the negatively-charged aspartic acid residue and replacing it with another negatively-charged residue may not be as effective at blocking receptor binding as if the aspartic acid were replaced with a positively-charged amino acid such as arginine, or uncharged residues such as serine or cysteine.

Recombinant production of an IL-15 mutein first requires isolation of a DNA clone (i.e., cDNA) that encodes an IL-15 mutein. cDNA clones are derived from primary cells or cell lines that express mammalian IL-15 polypeptides. First total cell mRNA is isolated, then a cDNA library is made from the mRNA by reverse transcription. A cDNA clone may be isolated and identified using the DNA sequence information provided herein to design a cross-pieces hybridization probe or PCR primer as described above. Such cDNA clones have the sequence of nucleic acids 1–486 of SEQ ID NO:1 and SEQ ID NO:2.

The isolated cDNA is preferably in the form of an open reading frame uninterrupted by internal nontranslated sequences, or introns. Genomic DNA containing the relevant nucleotide sequences that encode mammalian IL-15 polypeptides can also be used as a source of genetic information useful in constructing coding sequences. The isolated cDNA can be mutated utilizing techniques known in the art to provide IL-15 antagonist activity. Below, example 1 describes a specific method that can be used to prepare the IL-15 muteins.

Equivalent DNA constructs that encode various additions or substitutions of amino acid residues or sequences, or deletions of terminal or internal residues or sequences not needed for activity are encompassed by the invention. For example, N-glycosylation sites in IL-15 can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. The simian IL-15 protein comprises two such triplets, at amino acids 127–129 and 160–162 of SEQ ID NO:1. The human IL-15 protein comprises three such triplets, at amino acids 119–121, 127–129 and 160–162 of SEQ ID NO:2. Appropriate substitutions, additions or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846, hereby incorporated by reference.

Recombinant expression vectors include synthetic or cDNA-derived DNA fragments encoding an IL-15 mutein. The DNA encoding an IL-15 mutein is operably linked to a suitable transcriptional or translational regulatory or structural nucleotide sequence, such as one derived from mammalian, microbial, viral or insect genes. Examples of regulatory sequences include, for example, a genetic sequence having a regulatory role in gene expression (e.g., transcriptional promoters or enhancers), an optional operator sequence to control transcription, a sequence encoding suitable mRNA ribosomal binding sites, and appropriate sequences that control transcription and translation initiation and termination. Nucleotide sequences are operably linked when the regulatory sequence functionally relates to the structural gene. For example, a DNA sequence for a signal peptide (secretory leader) may be operably linked to a structural gene DNA sequence for an IL-15 mutein if the signal peptide is expressed as part of a precursor amino acid sequence and participates in the secretion of an IL-15 mutein. Further, a promoter nucleotide sequence is operably linked to a coding sequence (e.g., structural gene DNA) if the promoter nucleotide sequence controls the transcription of the structural gene nucleotide sequence. Still further, a ribosome binding site may be operably linked to a structural gene nucleotide coding sequence (e.g. IL-15 mutein) if the ribosome binding site is positioned within the vector to encourage translation.

Suitable host cells for expression of an IL-15 mutein include prokaryotes, yeast or higher eukaryotic cells under the control of appropriate promoters. Prokaryotes include gram negative or gram positive organisms, for example *E. coli* or bacilli. Suitable prokaryotic hosts cells for transformation include, for example, *E. coli, Bacillus sibtilis, Salmonella typhimurium*, and various other species within the genera *Pseudomonas, Streptomyces*, and *Staphylococcus*. As discussed in greater detail below, examples of suitable host cells also include yeast such as *S. cerevisiae*, a mammalian cell line such as Chinese Hamster Ovary (CHO) cells, or insect cells. Cell-free translation systems could also be employed to produce an IL-15 mutein using RNAs derived from the DNA constructs disclosed herein. Appropriate cloning and expression vectors for use with bacterial, insect, yeast, and mammalian cellular hosts are described, for example, in Pouwels et al. *Cloning Vectors: A Laboratory Manual*, Elsevier, N.Y., 1985.

When an IL-15 mutein is expressed in a yeast host cell, the nucleotide sequence (e.g., structural gene) that encodes an IL-15 mutein may include a leader sequence. The leader sequence may enable improved extracellular secretion of translated polypeptide by a yeast host cell.

IL-15 muteins may be expressed in yeast host cells, preferably from the *Saccharomyces* genus (e.g., *S. cerevisiae*). Other genera of yeast, such as *Pichia* or *Kluyveromyces*, may also be employed. Yeast vectors will often contain an origin of replication sequence from a 2μ yeast plasmid, an autonomously replicating sequence (ARS), a promoter region, sequences for polyadenylation, and sequences for transcription termination. Preferably, yeast vectors include an origin of replication sequence and selectable marker. Suitable promoter sequences for yeast vectors include promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EP-A-73,657.

Yeast vectors can be assembled, for example, using DNA sequences from pBR322 for selection and replication in *E. coli* (Amp$^r$ gene and origin of replication). Other yeast DNA sequences that can be included in a yeast expression construct include a glucose-repressible ADH2 promoter and α-factor secretion leader. The ADH2 promoter has been described by Russell et al. (*J. Biol. Chem.* 258:2674, 1982) and Beier et al. (*Nature* 300:724, 1982). The yeast α-factor leader sequence directs secretion of heterologous polypeptides. The α-factor leader sequence is often inserted between the promoter sequence and the structural gene sequence. See, e.g., Kurjan et al., *Cell* 30:933, 1982; and Bitter et al., *Proc. Natl. Acad. Sci. USA* 81:5330, 1984. A leader sequence may be modified near its 3' end to contain one or more restriction sites. This will facilitate fusion of the leader sequence to the structural gene.

Yeast transformation protocols are known to those skilled in the art. One such protocol is described by Hinnen et al., *Proc. Natl. Acad. Sci. USA* 75:1929, 1978. The Hinnen et al. protocol selects for Trp+ transformants in a selective medium, wherein the selective medium consists of 0.67% yeast nitrogen base, 0.5% casamino acids, 2% glucose, 10 mg/ml adenine and 20 mg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 mg/ml adenine and 80 mg/ml uracil. Repression of the ADH2 promoter is lost when glucose is exhausted from the medium.

Alternatively, in a prokaryotic host cell, such as *E. coli*, the IL-15 mutein may include an N-terminal methionine residue to facilitate expression of the recombinant polypeptide in a prokaryotic host cell. The N-terminal Met may be cleaved from the expressed recombinant IL-15 mutein.

The recombinant expression vectors carrying the recombinant IL-15 mutein structural gene nucleotide sequence are transfected or transformed into a suitable host microorganism or mammalian cell line.

Expression vectors transfected into prokaryotic host cells generally comprise one or more phenotypic selectable markers. A phenotypic selectable marker is, for example, a gene encoding proteins that confer antibiotic resistance or that supply an autotrophic requirement, and an origin of replication recognized by the host to ensure amplification within the host. Other useful expression vectors for prokaryotic host cells include a selectable marker of bacterial origin derived from commercially available plasmids. This selectable marker can comprise genetic elements of the cloning vector pBR322 (ATCC 37017). pBR322 contains genes for ampicillin and tetracycline resistance and thus provides simple means for identifying transformed cells. The pBR322 "backbone" sections are combined with an appropriate promoter and a IL-15 mutein structural gene sequence. Other commercially available vectors include, for example, pKK223-3 (Pharmacia Fine Chemicals, Uppsala, Sweden) and pGEM1 (Promega Biotec, Madison, Wis., USA).

Promoter-sequences are commonly used for recombinant prokaryotic host cell expression vectors. Common promoter sequences include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EPA 36,776) and tac promoter (Sambrook et al., *Molecular Cloning: A Laboratory Manual*, Cold Spring Harbor Laboratory, (1989)). A particularly useful prokaryotic host cell expression system employs a phage λ P$_L$ promoter and a cI857ts thermolabile repressor sequence. Plasmid vectors available from the American Type Culture Collection that incorporate derivatives of the λ P$_L$ promoter include plasmid pHUB2 (resident in *E. coli* strain JMB9 (ATCC 37092)) and pPLc28 (resident in *E. coli* RR1 (ATCC 53082)).

Mammalian or insect host cell culture systems also could be employed to express recombinant IL-15 muteins. Examples of suitable mammalian host cell lines include the COS-7 lines of monkey kidney cells (Gluzman et al., *Cell* 23:175, (1981); ATCC CRL 1651), L cells, C127 cells, 3T3 cells (ATCC CCL 163), CHO cells, HeLa cells (ATCC CCL 2), and BHK (ATCC CRL 10) cell lines. Suitable mammalian expression vectors include nontranscribed elements such as an origin of replication, a promoter sequence, an enhancer linked to the structural gene, other 5' or 3' flanking nontranscribed sequences, such as ribosome binding sites, a polyadenylation site, splice donor and acceptor sites, and transcriptional termination sequences.

Transcriptional and translational control sequences in mammalian host cell expression vectors may be provided by viral sources. For example, commonly used mammalian cell promoter sequences and enhancer sequences are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a structural gene sequence in a mammalian host cell. Viral early and late promoters are particularly useful because both are easily obtained from a viral genome as a fragment that may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included.

Exemplary mammalian expression vectors can be constructed as disclosed by Okayama and Berg (*Mol. Cell. Biol.* 3:280, 1983). Additional useful mammalian expression vectors are described in U.S. patent application Ser. No. 07/480, 694 filed Feb. 14, 1990 and U.S. Pat. No. 5,350,683.

Purification of Recombinant IL-15 Muteins

In general, IL-15 mutein polypeptides may be prepared by culturing transformed host cells under culture conditions necessary to express IL-15 mutein polypeptides. The resulting expressed mutein may then be purified from culture media or cell extracts. An IL-15 mutein may be concentrated using a commercially available protein concentration filter, for example, an Amicon or Millipore Pellicon ultrafiltration unit. With or without the concentration step, the culture media can be applied to a purification matrix such as a hydrophobic chromatography medium. Phenyl Sepharose® CL-4B (Pharmacia) is the preferred medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, gel filtration medium can be used.

Finally, one or more reverse-phase high performance liquid chromatography (RP-HPLC) steps employing hydrophobic RP-HPLC media, e.g., silica gel having pendant butyl or other aliphatic groups, can be employed to further purify IL-15 muteins. An S Sepharose (Pharmacia) cation exchange column may also be employed as a final buffer exchange step. Some or all of the foregoing conventional purification steps, in various combinations, can also be employed to provide a substantially homogeneous recombinant protein.

Recombinant protein produced in bacterial culture is usually isolated by initial disruption of the host cells, centrifugation, extraction from cell pellets if an insoluble polypeptide, or from the supernatant if a soluble polypeptide, followed by one or more concentration, salting-out, ion exchange or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express an IL-15 mutein as a secreted polypeptide. Secreted recombinant polypeptide from a yeast host cell fermentation can be purified by methods analogous to those disclosed by Urdal et al. (*J. Chromatog.* 296:171, 1984). Urdal et al. describe two sequential, reversed-phase HPLC steps for purification of recombinant human IL-2 on a preparative HPLC column.

Preferably, a mutein of IL-15 is used wherein at least one of the amino acid residues $Asp^{56}$ or $Gln^{156}$ of IL-15 (simian IL-15 having the sequence of amino acid residues 49–162 shown in SEQ ID NO:1 or human IL-15 having the sequence of amino acid residues 49–162 shown in SEQ ID NO:2) is deleted or substituted with a different naturally-occurring amino acid residue. Any combination of substitutions and/or deletions can be made. For example, $Asp^{56}$ can be deleted while $Gln^{156}$ is substituted with any other amino acid, or both $Asp^{56}$ and $Gln^{156}$ are each substituted with the same or different amino acid moiety. Further, $Asp^{56}$ can be substituted with any amino acid while $Gln^{156}$ is deleted. Generally, substitution muteins are preferred, and more preferred are those that do not severely affect the natural folding of the IL15 molecule. Substitution muteins preferably include those wherein $Asp^{56}$ is substituted by serine or cysteine; or wherein $Gln^{156}$ is substituted by serine or cysteine, or wherein both $Asp^{56}$ and $Gln^{156}$ are each substituted with a serine or cysteine. Examples of deletion muteins include those wherein $Asp^{56}$ and $Gln^{156}$ of mature IL-15 are both deleted; wherein only $Asp^{56}$ is deleted; or wherein only $Gln^{156}$ is deleted. It is possible that other amino acid residues in the region of either $Asp^{56}$ and $Gln^{156}$ can be substituted or deleted and still have an effect of preventing signal transduction through either or both of the β- or γ-subunits of the IL-15 receptor complex. Therefore, the invention further encompasses muteins wherein amino acid residues within the region of $Asp^{56}$ and $Gln^{156}$ are either substituted or deleted, and that possess IL-15 antagonist activity. Such muteins can be made using the methods described herein and can be assayed for IL-15 antagonist activity using conventional methods. Further description of a method that can be used to create the IL-15 muteins according to the invention is provided in Example 1.

Conjugated IL-15 Molecules and IL-15 Muteins

The mature IL-15 polypeptides disclosed herein (mature simian IL-15 comprising the sequence of amino acids 49–162 of SEQ ID NO:1 and mature human IL-15 having the sequence of amino acid residues 49–162 shown in SEQ ID NO:2), as well as the IL-15 muteins, may be modified by forming covalent or aggregative conjugates with other chemical moieties. Such moieties can include PEG, mPEG, dextran, PVP, PVA, polyamino acids such as poly-L-lysine or polyhistidine, albumin and gelatin at specific sites on the IL-15 molecule that can interfere with binding of IL-15 to the β- or γ-chains of the IL-15 receptor complex, while maintaining the high affinity of IL-15 for the IL-15Rα. Additionally, IL-15 can be specifically glycosylated at sites that can interfere with binding of IL-15 to the β- or γ-chains of the IL-15 receptor complex, while maintaining the high affinity of IL-15 for the IL-15Rα. Preferred groups for conjugation are PEG, dextran and PVP. Most preferred for use in the invention is PEG, wherein the molecular weight of the PEG is preferably between about 1,000 to about 20,000. A molecular weight of about 5000 is preferred for use in conjugating IL-15, although PEG molecules of other weights would be suitable as well. A variety of forms of PEG are suitable for use in the invention. For example, PEG can be used in the form of succinimidyl succinate PEG (SS-PEG) which provides an ester linkage that is susceptible to hydrolytic cleavage in vivo, succinimidyl carbonate PEG (SC-PEG) which provides a urethane linkage and is stable against hydrolytic cleavage in vivo, succinimidyl propionate PEG (SPA-PEG) provides an ether bond that is stable in vivo, vinyl sulfone PEG (VS-PEG) and maleimide PEG (Mal-PEG) all of which are commercially available from Shearwater Polymers, Inc. (Huntsville, Ala.). In general, SS-PEG, SC-PEG and SPA-PEG react specifically with lysine residues in the polypeptide, whereas VS-PEG and Mal-PEG each react with free cysteine residues. However, Mal-PEG is prone to react with lysine residues at alkaline pH. Preferably, SC-PEG and VS-PEG are preferred, and SC-PEG is most preferred due to its in vivo stability and specificity for lysine residues.

The PEG moieties can be bonded to IL-15 in strategic sites to take advantage of PEG's large molecular size. As described above, PEG moieties can be bonded to IL-15 by utilizing lysine or cysteine residues-naturally occurring in the protein or by site-specific PEGylation. One method of site specific PEGylation is through methods of protein engineering wherein cysteine or lysine residues are introduced into IL-15 at specific amino acid locations. The large molecular size of the PEG chain(s) conjugated to IL-15 is believed to block the region of IL-15 that binds to the β- and/or γ-subunits but not the α-subunit of the IL-15 receptor complex. Conjugations can be made by a simple addition reaction wherein PEG is added to a basic solution containing IL-15. Typically, PEGylation is carried out at either (1) about pH 9.0 and at molar ratios of SC-PEG to lysine residue of approximately 1:1 to 100:1, or greater, or (2) at about pH 7.0 and at molar ratios of VS-PEG to cysteine residue of approximately 1:1 to 100:1, or greater.

Characterization of the conjugated PEGylated. IL-15 molecules can be performed by SDS-PAGE on a 4–20% gradient polyacrylamide gel, available from Novex Corp., San Diego, Calif. Conventional silver staining may be employed, or conventional Western blotting techniques can be utilized for highly PEGylated proteins that are not visualized easily by silver staining. Purification of the PEGylated IL-15 molecules can be performed using size exclusion chromatography, dialysis, ultrafiltration or affinity purification.

The extent of modification and heterogeneity of PEGylated IL-15 can be determined using conventional matrix assisted laser desorption ionization mass spectrometry (MALDI). Since human IL-15 has a molecular weight of about 13,000 and by using PEG having a molecular weight of 5000, MALDI indicates that preparations weighing 13,000 are unPEGylated, those weighing 18,000 indicate that 1 molecule of IL-15 is bonded to one PEG molecule; those weighing 23,000 signify that one IL-15 molecule is bound with two PEG molecules, etc.

Monoclonal Antibodies Against IL-15

Alternatively, an antagonist according to the invention can take the form of a monoclonal antibody against IL-15 that interferes with the binding of IL-15 to any of the α-, β- or γ-subunits of the IL-15 receptor complex. Within one aspect of the invention, IL-15, including derivatives thereof, as well as portions or fragments of these proteins such as IL-15 peptides, can be used to prepare antibodies that specifically bind to IL-15. Within the context of the invention, the term "antibodies" should be understood to include polyclonal antibodies, monoclonal antibodies, fragments thereof such as F(ab')2 and Fab fragments, as well as recombinantly produced binding partners. The affinity of a monoclonal antibody or binding partner may be readily determined by one of ordinary skill in the art (see Scatchard, Ann. N.Y. Acad. Sci., 51: 660–672 (1949)). Specific examples of such monoclonal antibodies are provided in Example 2 herein.

In general, monoclonal antibodies against IL-15 can be generated using the following procedure. Purified IL-15, a fragment thereof, synthetic peptides or cells that express IL-15 can be used to generate monoclonal antibodies against IL-15 using techniques known per se, for example, those techniques described in U.S. Pat. No. 4,411,993. Briefly, mice are immunized with IL-15 as an immunogen emulsified in complete Freund's adjuvant or RIBI adjuvant (RIBI Corp., Hamilton, Mont.), and injected in amounts ranging from 10–100 μg subcutaneously or intraperitoneally. Ten to twelve days later, the immunized animals are boosted with additional IL-15 emulsified in incomplete Freund's adjuvant. Mice are periodically boosted thereafter on a weekly to bi-weekly immunization schedule. Serum samples are periodically taken by retro-orbital bleeding or tail-tip excision to test for IL-15 antibodies by dot blot assay, ELISA (Enzyme-Linked Immunosorbent Assay) or inhibition of IL-15 activity on CTLL-2 cells.

Following detection of an appropriate antibody titer, positive animals are provided an additional intravenous injection of IL-15 in saline. Three to four days later, the animals are sacrificed, spleen cells harvested, and spleen cells are fused to a murine myeloma cell line, e.g., NS1 or preferably P3×63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused myeloma cells and myeloma hybrids.

The hybridoma cells are screened by ELISA for reactivity against purified IL-15 by adaptations of the techniques disclosed in Engvall et al., Immunochem. 8:871, 1971 and in U.S. Pat. No. 4,703,004. A preferred screening technique is the antibody capture technique described in Beckmann et al., (J. Immunol. 144:4212, 1990). Positive hybridoma cells can be injected intraperitoneally into syngeneic Balb/c mice to produce ascites containing high concentrations of anti-IL-15 monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to protein A or protein G can also be used, as can affinity chromatography based upon binding to IL-15.

Other "antibodies" can be prepared utilizing the disclosure provided herein, and thus fall within the scope of the invention. Procedures used to generate humanized antibodies can be found in U.S. Pat. No. 4,816,567 and WO 94/10332; procedures to generate microbodies can be found in WO 94/09817; and procedures to generate transgenic antibodies can be found in GB 2 272 440, all of which are incorporated herein by reference.

To determine which monoclonal antibodies are antagonists, use of a screening assay is preferred. A CTLL-2 proliferation assay is preferred for this purpose. See, Gillis and Smith, Nature 268:154 (1977), which is incorporated herein by reference.

The antagonists according to the invention find use, as described above and in more detail below, in promoting allograft survival and in treating patients with graft versus host disease. Another credible use for the antagonists include the treatment of late phase HTLV (human T-cell lymphotrophic virus) I-induced adult T-cell leukemia-lymphoma. See Burton et al., Proc. Natl. Acad. Sci., 91:4935 (1994). Other credible uses include ability to prevent B cell or T-cell stimulation in vitro, study receptor-ligand interaction, in diagnostic kits for infectious disease and disorders of the gastrointestinal tract. By virtue of the activity of the antagonists according to the invention, new methods of treating certain diseases are within the scope of the invention. For example, there is disclosed a method for preventing allograft rejection in a patient in need thereof, and a method of treating GVHD in a patient in need thereof, each method comprising the step of administering a pharmaceutical composition comprising an amount of an IL-15 antagonist effective to inhibit IL-15 activity, and a pharmaceutically acceptable carrier or diluent. Similar methods are useful for treating other diseases whereby the target cells (the cells that are believed to be primarily responsible for the diseased condition, or a symptom of the diseased condition) are expressing the IL-15 receptor complex and where a blockade or inhibition of signal transduction through the β- or γ-subunits of the IL-15 receptor is desired. Such disease states may be treatable with the antagonists of the invention upon learning that the target cells express the IL-15 receptor complex. Indeed, in addition to GVHD and allograft rejection, such disease states may include, for example, lymphomas, carcinomas, leukemias, rhabdosarcomas, and certain autoimmune disorders such as rheumatoid arthritis. The fact that the foregoing list is not exhaustive of all disease states wherein the target cells express the required IL-15-receptor complex, should not be construed as limiting the scope of the invention.

As described above, another embodiment of the invention is the nucleic acids that encode the IL-15 muteins of the invention. Such nucleic acids comprise either RNA or the cDNA having the nucleotide sequence from 144 to 486 of SEQ ID NO:1 and 144 to 486 of SEQ ID NO:2. Further within the scope of the invention are expression vectors that comprise a cDNA encoding an IL-15 mutein and host cells transformed or transfected with such expression vector. Transformed host cells are cells that have been transformed or transfected with a recombinant expression vector using standard procedures. Expressed mammalian IL-15 will be located within the host cell and/or secreted into culture supernatant, depending upon the nature of the host cell and the gene construct inserted into the host cell. Pharmaceutical compositions comprising any of the above-described IL-15 antagonists also are encompassed by this invention.

Administration of Antagonists of IL-15

The present invention provides methods of using pharmaceutical compositions comprising an effective amount of IL-15 antagonist in a suitable diluent or carrier. An IL-15 antagonist of the invention can be formulated according to known methods used to prepare pharmaceutically useful compositions. An IL-15 antagonist can be combined in admixture, either as the sole active material or with other known active materials, with pharmaceutically suitable diluents (e.g., Tris-HCl, acetate, phosphate), preservatives (e.g., Thimerosal, benzyl alcohol, parabens), emulsifiers, solubilizers, adjuvants and/or carriers. Suitable carriers and their formulations are described in Remington's Pharmaceutical Sciences, 16th ed. 1980, Mack Publishing Co. In addition, such compositions can contain an IL-15 antagonist complexed with polyethylene glycol (PEG), metal ions, or incorporated into polymeric compounds such as polyacetic acid, polyglycolic acid, hydrogels, etc., or incorporated into liposomes, microemulsions, micelles, unilamellar or multi-lamellar vesicles, erythrocyte ghosts or spheroblasts. Such compositions will influence the physical state, solubility, stability, rate of in vivo release, and rate of in vivo clearance of an IL-15 antagonist. An IL-15 antagonist can also be conjugated to antibodies against tissue-specific receptors, ligands or antigens, or coupled to ligands of tissue-specific receptors.

The IL-15 antagonist of the invention can be administered topically, parenterally, rectally or by inhalation. The term "parenteral" includes subcutaneous injections, intravenous, intramuscular, intrasternal injection, or infusion techniques. These compositions will typically contain an effective amount of an IL-15 antagonist, alone or in combination with an effective amount of any other active material. Such dosages and desired drug concentrations contained in the compositions may vary depending upon many factors, including the intended use, patient's body weight and age, and route of administration. Preliminary doses can be determined according to animal tests, and the scaling of dosages for human administration can be performed according to art-accepted practices.

In addition to the above, the following examples are provided to illustrate particular embodiments and not to limit the scope of the invention.

EXAMPLE 1

Muteins of IL-15

This example describes a method for obtaining muteins of mature, or native, IL-15 that function as antagonists of IL-15. IL-15, like IL-2, is able to bind to and signal through the IL-2Rβγ complex, and as such, is proposed to share structural similarities to IL-2. The equivalent residues in IL-15 that have previously been shown in IL-2 to be critical for interaction with the IL-2Rβ- and γ-chain (Zurawski, et al., *EMBO J.*, 12(13):5113 (1993)) were determined by best-fit sequence alignment to be aspartic acid, residue 56 (Asp) for the β-chain, and glutamine, residue 156 (Gln) for the γ-chain (amino acid numbering is based on the sequence of the peptide as shown by amino acid residues 1–162 of SEQ ID NOS:1 and 2).

Oligonucleotide primers were designed that would amplify human IL-15 and introduce a codon encoding either a serine or a cysteine at either residue 56 or 156. Two separate rounds of PCR amplification were performed for the construction of each mutant (see diagram below). In the primary PCR reaction, amplification was with primer pairs that either introduced the appropriate mutation, or amplified the mature sequence. In the secondary PCR reaction, material from the first round was reamplified with a primer set that introduced restriction sites for cloning into the pαADH2 yeast expression vector pIXY456. See, Price et al., *Gene*, 55:287 (1987) and Price et al., *Meth. Enzym.* 185:308 (1990).

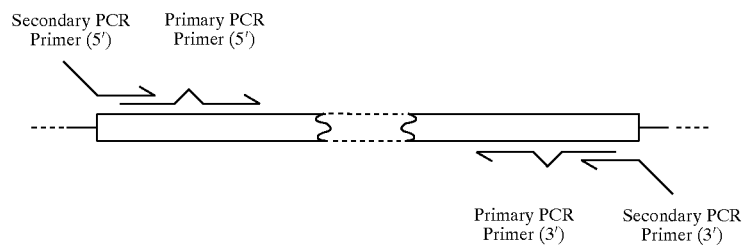

The table below lists the pairs of oligonucleotide primers used for the primary amplification of each mutein. The oligonucleotides NTFIL15B (5' primer) and NCTFIL15F (3' primer) were used for the primary amplification when maintenance of the mature sequence was desired.

| Clone Name | Amino Acid Substitutions | | Expected Phenotype | Primary PCR 5' Primer | Primary PCR 3' Primer |
|---|---|---|---|---|---|
| | D56 | Q156 | | | |
| DQ | D | Q | mature | NTFIL15B | NCTFIL15F |
| SQ | S | Q | β−/γ+ | D56SER5 | NCTFIL15F |
| DS | D | S | β+/γ− | NTFIL15B | Q156SER3 |
| SS | S | S | β−/γ− | D56SER5 | Q156SER3 |
| CQ | C | Q | β−/γ+ | D56CYS5 | NCTFIL15F |
| DC | D | C | β+/γ− | NTFIL15B | Q156CYS3 |
| CC | C | C | β−/γ− | D56CYS5 | Q156CYS3 |

| Primer Name | Sequence | |
|---|---|---|
| Primary PCR | | |
| D56Cys5 | (5'-AATGTAATAAGTTGTTTGAAAAAAATT-3') | SEQ ID NO: 3 |
| D56Ser5 | (5'-AATGTAATAAGTTCTTTGAAAAAAATT-3') | SEQ ID NO: 4 |
| Q156Cys3 | (5'-GTfGATGAACATGCAGACAATATG-3') | SEQ ID NO: 5 |
| Q156Ser3 | (5'-GTTGATGAACATAGAGACAATATG-3') | SEQ ID NO: 6 |
| NTFTL15B | (5'-GTCCTCGCAACTAAGTCGACTAACTGGGT-GAATGTAATA-3') | SEQ ID NO:7 |

-continued

| Primer Name | Sequence | |
|---|---|---|
| NCTFIL15F Secondary PCR | (5'-GAGTCATTCTCGACTTGCGGCCGCACCAG-AAGTGTTGATGAACAT-3') | SEQ ID NO: 8 |
| IL15PIXYF5 | (5'-AATATGGTACCTTTGGATAAAAGAGACTA-CAAGGACGACGATGACAAGAACTGGGTGAAT-GTAATAAGT-3') | SEQ ID NO: 9 |
| IL15PIXY3 | (5'-GCGATATATCCATGGTCAAGAAGTGTTGA-TGAACAT-3') | SEQ ID NO: 10 |

Alternatively, oligonucleotide NTFIL15B could be substituted with oligonucleotide IL15PIXYF5, and oligonucleotide NCTFIL15F could be substituted with oligonucleotide IL15PIXY3. Primary PCR amplification was performed in 100 µl of 1×Taq polymerase buffer (Boehringer) containing 250 µM dNTPs and 50 pmol of the 5' and 3' oligonucleotide primer. The DNA template used was approximately 50 ng of pIXY764. Vector pIXY764 is similar to the above-described vector pIXY456 that contains DNA encoding human flag IL-15, wherein the N-linked glycosylation sites of human IL-15 have been inactivated using procedures described supra. Reaction mixtures were overlaid with mineral oil, and heated to 94° C. in the thermal cycler for 5 minutes before the addition of 2 Units of Taq polymerase (Boehringer) and the commencement of thermal cycling. Cycling conditions were denaturation at 94° C. for 45 seconds, annealing at 45° C. for 45 seconds and extension at 72° C. for 1 minute, for a total of 30 cycles.

Approximately 20 ng of gel purified product from the primary amplification was used as the template for the secondary PCR amplification. All constructs were amplified with IL15PIXYF5 and IL15PIXY3 using the same buffer conditions as before. Cycling conditions were denaturation at 94° C. for 45 seconds, annealing at 60° C. for 45 seconds and extension at 72° C. for 1 minute, for a total of 20 cycles.

Amplification products were gel purified and digested with Asp718 (Boehringer) and NcoI (New England Biolabs) overnight at 37° C. in 1× Boehringer buffer B. The restriction products were ligated into a pIXY456 yeast expression vector that had been digested with Asp718 and NcoI. This DNA was used to transform DH10βE. coli cells by electroporation.

Plasmid DNA from single transformants was sequenced to confirm sequence integrity, and used to transform XV2181 S. cerevisiae. Biological activity was assayed using yeast supernatant following 30 hour induction.

These experiments employed a PCR-based strategy for the mutagenesis on account of the mutagenesis sites being located near the ends of the IL-15 gene. However, these, and any other single or multiple point mutations could be introduced by conventional site-directed mutagenesis techniques.

EXAMPLE 2

Monoclonal Antibodies Against IL-15

This example describes the method used to obtain three anti-IL-15 monoclonal antibodies that function as antagonists of IL-15. All methods used are conventional techniques, except where noted.

Balb/c mice were injected intraperitoneally on two occasions at 3 week intervals with 10 ug of yeast-derived human IL-15 in the presence of RIBI adjuvant (RIBI Corp., Hamilton, Mont.). Mouse sera was then assayed by conventional dot blot technique, antibody capture (ABC) and neutralization assay (CTLL-2 assay) to determine which animal was best to fuse. Three weeks later, mice were given an intravenous boost of 3 µg of human IL-15 suspended in sterile PBS. Three days later, mice were sacrificed and spleen cells were fused with Ag8.653 myeloma cells (ATCC) following established protocols. Briefly, Ag8.653 cells were washed several times in serum-free media and fused to mouse spleen cells at a ratio of three spleen cells to one myeloma cell. The fusing agent was 50% PEG: 10% DMSO (Sigma). Fusion was plated out into twenty 96-well flat bottom plates (Corning) containing HAT supplemented DMEM media and allowed to grow for eight days. Supernatants from resultant hybridomas were collected and added to a 96-well plate for 60 minutes that had been first coated with goat anti-mouse Ig. Following washes, $^{125}$I-IL-15 was added to each well, incubated for 60 minutes at room temperature, and washed four times. Positive wells were subsequently detected by autoradiography at −70° C. using Kodak X-Omat S film. Positive clones were grown in bulk culture and supernatants were subsequently purified over a Protein A column (Pharmacia). The clones designated as M110, M111 and M112 were each subsequently isotyped as IgG1 monoclonal antibodies. Hybridomas producing monoclonal antibodies M110, M111 and M112 have been deposited with the American Type Culture Collection Rockville, Md., USA (ATCC) on Mar. 13, 1996 and assigned accession numbers HB-12061, HB-12062 and HB-12063, respectively. All deposits were made according to the terms of the Budapest Treaty.

Monoclonal antibodies generated can be assayed for IL-15 antagonist activity using the CTLL-2 assay as essentially described by Gillis, et al., Id.

EXAMPLE 3

Modified IL-15 Molecules

This example describes a method for obtaining modified IL-15 molecules that function as IL-15 antagonists.

PEGylated IL-15

All conjugation reactions were performed with PEG, 5000 molecular weight, that was obtained in forms of succinimidyl succinate PEG (SS-PEG), succinimidyl carbonate PEG (SC-PEG), VS-PEG and Mal-PEG from Shearwater Polymers, Inc. (Huntsville, Ala.). Both of the SS-PEG and SC-PEG react with the ε-amino group of lysine, forming a hydrolytically unstable ester linkage in the case of SS-PEG, and a hydrolytically stable urethane linkage in the case of SC-PEG. PEGylation was performed in 50 nM $NaH_2PO_4$ at pH 9.0 for SS-PEG and SC-PEG; and at pH 7.0 for reactions containing VS-PEG and Mal-PEG. The reactions proceeded in 0.5 ml volumes at 100 μg/ml. In each reaction, PEG was added to the reaction mixtures at molar ratios of PEG to lysine of 1:1, 3:1, 10:1 and 100:1 (there are 9 lysine residues in each simian IL-15 molecule). The reactions proceeded overnight at 4° C.

Characterization of PEGylated simian IL-15 was made by SDS-PAGE on 4–20% gradient polyacrylamide gels (Novex, San Diego, Calif.). Conventional silver staining techniques were used for unmodified IL-15 proteins loaded at approximately 0.5 μg/lane. Highly PEGylated simian IL-15 proteins required loading larger quantities of protein onto the gel for visualization. Western blots were also used to characterize the highly PEGylated IL-15. In these experiments, PEGylated simian IL-15 was separated by SDS-PAGE, transferred to nitrocellulose membrane, incubated with monoclonal antibody M111, followed by incubation with goat anti-mouse HRP, and finally visualized with 4 CN Membrane Peroxidase Substrate System (Kirkegaard & Perry Laboratories, Gaithersburg, Md.). PEGylated simian IL-15 was also characterized by size exclusion chromatography (SEC) HPLC with a Biosil SEC-250 sizing column (Biorad, Richmond, Calif.) according to conventional techniques.

SC-PEGylated FLAG-simian IL-15 was tested for its ability to bind to transfected COS cells that expressed IL-15 α-, or β- and γ-receptor subunits on the cell membrane surface. The PEGylated IL-15 inhibited radiolabeled IL-15 binding to COS cells expressing the IL-15R α-subunit indicating that PEGylated IL-15 competes for IL-15Rα-subunit binding. Further, the PEGylated IL-15 did not inhibit binding of radiolabeled IL-15 to COS cells expressing β- and γ-preceptor subunits indicating that the PEGylated IL-15 does not bind to β- and/or γ-receptor subunits of the IL-15 receptor complex. Thus, PEGylated IL-15 prevents endogenous IL-15 from effecting signal transduction through the β- and γ-receptor subunits of the IL-15 receptor complex.

EXAMPLE 4

Inhibition of IL-15 Activity in CTLL-2 Assay

This example further illustrates a method for determining the prevention by the antagonists according to the invention of signal transduction of IL-15 through the β- and γ-receptor subunits of the IL-15 receptor complex.

Antagonist activity of monoclonal antibodies, PEGylated IL-15 and IL-15 muteins can be assessed using a modified CTLL-2 cell $^3$H-Thymidine incorporation assay (Gillis, et al., Id.). Serial dilutions of antagonist can be made in 96-well flat-bottom tissue culture plates (Costar, Cambridge, Mass.) in DMEM medium (supplemented with 5% FCS, NEAA, NaPyruvate, HEPES pH 7.4, 2-me, PSG) at a final volume of 50 μl. A sub-optimal amount of IL-15 (final concentration of 20–40 pg/ml) then is added to all assay wells (5 μl/well) after serial dilution of samples and prior to addition of cells. Washed CTLL-2 cells are added (about 2000 per well in 50 μl) and the plates are incubated for 24 hours at 37° C. in a humidified atmosphere of 10% $CO_2$ in air. This was followed by a five hour incubation with 0.5 μCi of $^3$H-Thymidine (25 Ci/mMol, Amersham, Arlington Heights, Ill.). The cultures then are harvested on glass fiber filters and counted by avalanche gas ionization either on a multidetector direct beta counter (Matrix 96, Packard Instrument Company, Meridien, Conn.) or on a beta scintillation counter. The counts per minute (CPM) generated by the assay are converted to percent inhibition and the percent inhibition values of each titrated antagonist sample are used to calculate antagonist activity in units/ml.

Data showing the concentration needed to neutralize 40 pg/ml of IL-15 in a CTLL inhibition assay is provided in Table I below. Table II below shows the activity of IL-15 (agonist activity) and IL-15 antagonists in CTLL and CTLL inhibition assays.

TABLE I

Specific Activity of IL-15 Antagonists

The concentration of antagonist required to neutralize 40 pg/ml IL-15 in CTLL inhibition assay:

| antagonist | concentration | method of protein determination |
|---|---|---|
| huIL-15 muteins | 848–2560 pg/ml | ELISA/estimated from AAA |
| M110, M111 | 5 ng/ml | OD |
| PEGhuIL-15 D56C | 7.7 ng/ml | estimated from AAA |
| M112 | 40 ng/ml | OD |
| PEGf-s-IL15 | 140–196 ng/ml | AAA |

OD = optical density absorbence at 280 nm; extinction coefficient of 1.35
AAA = amino acid analysis
PEGf-s-IL15 = PEGylated flag simian IL-15

TABLE II

Activity of IL-15 and IL-15 Antagonists in CTLL and CTLL Inhibition Assays

| sample | CTLL Assay units/ml (Agonist Activity) | CTLL Inhibition Assay units/ml (Antagonist Activity) |
|---|---|---|
| IL-15 | $7.09 \times 10^5$ | 279 |
| IL-15-Q156C | — | $3 \times 10^6$ |
| IL-15-Q156S | — | $1.5 \times 10^6$ |
| IL-15-D56C | — | $2 \times 10^6$ |
| IL-15-D56C-Q156C | — | $2 \times 10^5$ |
| IL-15-D56C-Q156S | — | $7 \times 10^5$ |
| IL-15-D56S | — | $2.2 \times 10^5$ |
| IL-15-D56S-Q156S | — | $7.2 \times 10^5$ |
| vector control | — | 1141 |
| IL-15 | $3.7 \times 10^8$ | NA |
| PEG-IL-15 | — | $2.3 \times 10^6$ |
| PEG-IL-15-D56C | — | $7.96 \times 10^6$ |
| IL-15-D56C | — | $5 \times 10^6$ |
| IL-15 | $5.6 \times 10^8$ | NA |
| PEG-IL-15 | NA | $1.7 \times 10^5$ |

Q156C = $Gln^{156}$ substituted with Cys
Q156S = $Gln^{156}$ substituted with Ser
D56C = $Asp^{56}$ substituted with Cys
D56S = $Asp^{56}$ substituted with Ser
NA: not assayed

What is claimed is:

1. An antagonist of interleukin-15 (IL-15) activity comprising IL-15 or a mutein thereof, conjugated with a chemical group that sterically interferes with the ability of IL-15 to transduce a signal through the IL-15 receptor complex, wherein said antagonist is capable of binding to said IL-15 receptor complex.

2. The antagonist of claim 1 wherein said IL-15 is native.

3. The antagonist of claim 2 wherein the native IL-15 comprises the sequence of amino acids 49–162 of SEQ ID NO: 1 or 49–162 of SEQ ID NO: 2.

4. An antagonist of interleukin-15 (IL-15) activity comprising native IL-15 comprising the sequence of amino acids 49–162 of SEQ ID NO: 2 conjugated with a chemical group that sterically interferes with the ability of IL-15 to transduce a signal through the IL-15 receptor complex, wherein said antagonist is capable of binding to said IL-15 receptor complex.

5. The antagonist of claim 1 wherein a mutein of IL-15 is conjugated with a chemical group that sterically interferes with the ability of IL-15 to transduce a signal through the IL-15 receptor complex.

6. The antagonist of claim 5 wherein the mutein comprises at least one deletion or substitution with a different naturally-occurring amino acid residue at a position corresponding to amino acid residue $Asp^{56}$ or $Gln^{156}$ of SEQ ID NOs: 1 or 2.

7. An antagonist of interleukin-15 (IL-15) activity comprising a mutein corresponding to amino acids 49–162 of SEQ ID: 2, wherein either or both of $Asp^{56}$ or $Gln^{156}$ are substituted with serine or cysteine, conjugated with a chemical group that sterically interferes with the ability of IL-15 to transduce a signal through the IL-15 receptor complex.

8. The antagonist of claim 7 wherein $Asp^{56}$ is substituted with serine or cysteine.

9. The antagonist of claim 7 wherein $Gln^{156}$ is substituted with serine or cysteine.

10. The antagonist of claim 1 wherein the chemical group is selected from the group consisting of PEG, mPEG, PVP, dextran, PVA, poly amino acids, albumin, and gelatin.

11. The antagonist of claim 10 wherein the chemical group is selected from the group consisting of PEG, PVP, and dextran.

12. The antagonist of claim 11 wherein the chemical group is PEG having a molecular weight of between about 1,000 and about 20,000.

13. The antagonist of claim 3 wherein the IL-15 is covalently bonded to PEG having a molecular weight of between about 1,000 and about 20,000.

14. The antagonist of claim 6 wherein the mutein is covalently bonded to PEG having a molecular weight between about 1000 and about 20,000.

15. The antagonist of claim 12 wherein the PEG has a molecular weight of about 5,000.

16. The antagonist of claim 12 wherein the PEG is selected from the group consisting of SS-PEG, SC-PEG, SPA-PEG, VS-PEG, and Mal-PEG.

17. The antagonist of claim 16 wherein the PEG is SC-PEG.

18. A composition comprising a pharmaceutically acceptable carrier or diluent and an antagonist according to claim 1.

19. A composition comprising a pharmaceutically acceptable carrier or diluent and an antagonist according to claim 3.

20. A composition comprising a pharmaceutically acceptable carrier or diluent and an antagonist according to claim 6.

21. A composition comprising a pharmaceutically acceptable carrier or diluent and an antagonist according to claim 12.

22. A method for treating a patient having symptoms of organ transplant rejection, graft-versus-host disease, autoimmune disease, rheumatoid arthritis, inflammatory bowel disease, lymphoma, carcinoma, leukemia, rhabdosarcoma, a dermatologic disorder, insulin-dependent diabetes mellitus, an ocular disorder, idiopathic nephrotic syndrome, or idiopathic membranous nephropathy comprising administering to the patient a pharmaceutical composition according to claim 18.

23. The method of claim 22 wherein the patient has symptoms of rheumatoid arthritis, lymphoma, carcinoma, leukemia, or a dermatologic disorder.

24. A method for treating a patient having symptoms of rheumatoid arthritis, lymphoma, carcinoma, leukemia, or a dermatologic disorder comprising administering to the patient a pharmaceutical composition according to claim 19.

25. A method for treating a patient having symptoms of rheumatoid arthritis, lymphoma, carcinoma, leukemia, or a dermatologic disorder comprising administering to the patient a pharmaceutical composition according to claim 20.

26. A method for treating a patient having symptoms of rheumatoid arthritis, lymphoma, carcinoma, leukemia, or a dermatologic disorder comprising administering to the patient a pharmaceutical composition according to claim 21.

27. A method for treating a patient having the symptoms of graft-versus-host disease or to prolong allograft survival comprising administering to the patient a pharmaceutical composition according to claim 19.

28. A method for treating a patient having the symptoms of graft-versus-host disease or to prolong allograft survival comprising administering to the patient a pharmaceutical composition according to claim 20.

29. A method for treating a patient having the symptoms of graft-versus-host disease or to prolong allograft survival comprising administering to the patient a pharmaceutical composition according to claim 21.

30. A method for making the antagonist of claim 1 comprising conjugating IL-15 or a mutein of IL-15 with a chemical group that sterically interferes with the ability of IL-15 to transduce a signal through the IL-15 receptor complex.

31. A method for reducing IL-15 activity comprising administering a composition according to claim 18.

32. A method for reducing IL-15 activity comprising administering a composition according to claim 19.

33. A method for reducing IL-15 activity comprising administering a composition according to claim 20.

34. A method for reducing IL-15 activity comprising administering a composition according to claim 21.

35. A method according to claim 31 wherein the composition is administered to a patient in need of such treatment.

36. A method according to claim 32 wherein the composition is administered to a patient in need of such treatment.

37. A method according to claim 33 wherein the composition is administered to a patient in need of such treatment.

38. A method according to claim 34 wherein the composition is administered to a patient in need of such treatment.

* * * * *

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
       (A) LENGTH: 489 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (ix) FEATURE:
       (A) NAME/KEY: CDS
       (B) LOCATION: 1..342

(xi) SEQUENCE DESCRIPTION: SEQ ID NO: 1:

```
ATG AGA ATT TCG AAA CCA CAT TTG AGA AGT ATT TCC ATC CAG TGC TAC       48
Met Arg Ile Ser Lys Pro His Leu Arg Ser Ile Ser Ile Gln Cys Tyr
 1               5                  10                  15

CTG TGT TTA CTT CTA AAG AGT CAT TTT CTA ACT GAA GCT GGC ATT CAT       96
Leu Cys Leu Leu Leu Lys Ser His Phe Leu Thr Glu Ala Gly Ile His
                20                  25                  30

GTC TTC ATT TTG GGC TGT TTC AGT GCA GGG CTC CCT AAA ACA GAA GCC      144
Val Phe Ile Leu Gly Cys Phe Ser Ala Gly Leu Pro Lys Thr Glu Ala
         35                  40                  45

AAC TGG GTG AAT GTA ATA AGT GAT TTG AAA AAA ATT GAA GAT CTT ATT      192
Asn Trp Val Asn Val Ile Ser Asp Leu Lys Lys Ile Glu Asp Leu Ile
 50                  55                  60

CAA TCT ATG CAT ATT GAT GCT ACT TTA TAT ACA GAA AGT GAT GTT CAC      240
Gln Ser Met His Ile Asp Ala Thr Leu Tyr Thr Glu Ser Asp Val His
 65                  70                  75                  80

CCC AGT TGC AAG GTA ACA GCA ATG AAG TGC TTT CTC TTG GAG TTG CAA      288
Pro Ser Cys Lys Val Thr Ala Met Lys Cys Phe Leu Leu Glu Leu Gln
                 85                  90                  95

GTT ATT TCA CAT GAG TCC GGA GAT ACA GAT ATT CAT GAT ACA GTA GAA      336
Val Ile Ser His Glu Ser Gly Asp Thr Asp Ile His Asp Thr Val Glu
            100                 105                 110

AAT CTT ATC ATC CTA GCA AAC AAC ATC TTG TCT TCT AAT GGG AAT ATA      384
Asn Leu Ile Ile Leu Ala Asn Asn Ile Leu Ser Ser Asn Gly Asn Ile
        115                 120                 125

ACA GAA TCT GGA TGC AAA GAA TGT GAG GAA CTA GAG GAA AAA AAT ATT      432
Thr Glu Ser Gly Cys Lys Glu Cys Glu Glu Leu Glu Glu Lys Asn Ile
    130                 135                 140

AAA GAA TTT TTG CAG AGT TTT GTA CAT ATT GTC CAA ATG TTC ATC AAC      480
Lys Glu Phe Leu Gln Ser Phe Val His Ile Val Gln Met Phe Ile Asn
145                 150                 155                 160

ACT TCT TGA                                                          489
Thr Ser
```

(2) INFORMATION FOR SEQ ID NO: 2:

(i) SEQUENCE CHARACTERISTICS:
       (A) LENGTH: 489 base pairs
       (B) TYPE: nucleic acid
       (C) STRANDEDNESS: single
       (D) TOPOLOGY: linear (ii) MOLECULE TYPE: cDNA (ix) FEATURE:
    (A) NAME/KEY: CDS
    (B) LOCATION: 1..489

(xi) SEQUENCE DESCRIPTION: SEQ ID NO: 2:

```
ATG AGA ATT TCG AAA CCA CAT TTG AGA AGT ATT TCC ATC CAG TGC TAC        48
Met Arg Ile Ser Lys Pro His Leu Arg Ser Ile Ser Ile Gln Cys Tyr
 1               5                  10                  15

TTG TGT TTA CTT CTA AAC AGT CAT TTT CTA ACT GAA GCT GGC ATT CAT        96
Leu Cys Leu Leu Leu Asn Ser His Phe Leu Thr Glu Ala Gly Ile His
            20                  25                  30

GTC TTC ATT TTG GGC TGT TTC AGT GCA GGG CTT CCT AAA ACA GAA GCC       144
Val Phe Ile Leu Gly Cys Phe Ser Ala Gly Leu Pro Lys Thr Glu Ala
        35                  40                  45

AAC TGG GTG AAT GTA ATA AGT GAT TTG AAA AAA ATT GAA GAT CTT ATT       192
Asn Trp Val Asn Val Ile Ser Asp Leu Lys Lys Ile Glu Asp Leu Ile
50                  55                  60

CAA TCT ATG CAT ATT GAT GCT ACT TTA TAT ACG GAA AGT GAT GTT CAC       240
Gln Ser Met His Ile Asp Ala Thr Leu Tyr Thr Glu Ser Asp Val His
65                  70                  75                  80

CCC AGT TGC AAA GTA ACA GCA ATG AAG TGC TTT CTC TTG GAG TTA CAA       288
Pro Ser Cys Lys Val Thr Ala Met Lys Cys Phe Leu Leu Glu Leu Gln
                85                  90                  95

GTT ATT TCA CTT GAG TCC GGA GAT GCA AGT ATT CAT GAT ACA GTA GAA       336
Val Ile Ser Leu Glu Ser Gly Asp Ala Ser Ile His Asp Thr Val Glu
            100                 105                 110

AAT CTG ATC ATC CTA GCA AAC AAC AGT TTG TCT TCT AAT GGG AAT GTA       384
Asn Leu Ile Ile Leu Ala Asn Asn Ser Leu Ser Ser Asn Gly Asn Val
        115                 120                 125

ACA GAA TCT GGA TGC AAA GAA TGT GAG GAA CTG GAG GAA AAA AAT ATT       432
Thr Glu Ser Gly Cys Lys Glu Cys Glu Glu Leu Glu Glu Lys Asn Ile
130                 135                 140

AAA GAA TTT TTG CAG AGT TTT GTA CAT ATT GTC CAA ATG TTC ATC AAC       480
Lys Glu Phe Leu Gln Ser Phe Val His Ile Val Gln Met Phe Ile Asn
145                 150                 155                 160

ACT TCT TGA                                                           489
Thr Ser
```

(2) INFORMATION FOR SEQ ID NO: 3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 3:

AATGTAATAA GTTGTTTGAA AAAAATT                                         27

(2) INFORMATION FOR SEQ ID NO: 4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

AATGTAATAA GTTCTTTGAA AAAAATT                                              27

(2) INFORMATION FOR SEQ ID NO: 5:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (xi) SEQUENCE DESCRIPTION: SEQ ID NO: 5:

GTTGATGAAC ATGCAGACAA TATG                                                 24

(2) INFORMATION FOR SEQ ID NO: 6:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (xi) SEQUENCE DESCRIPTION: SEQ ID NO: 6:

GTTGATGAAC ATAGAGACAA TATG                                                 24

(2) INFORMATION FOR SEQ ID NO: 7:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (xi) SEQUENCE DESCRIPTION: SEQ ID NO: 7:

GTCCTCGCAA CTAAGTCGAC TAACTGGGTG AATGTAATA                                 39

(2) INFORMATION FOR SEQ ID NO: 8:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (xi) SEQUENCE DESCRIPTION: SEQ ID NO: 8:

GAGTCATTCT CGACTTGCGG CCGCACCAGA AGTGTTGATG AACAT                          45

(2) INFORMATION FOR SEQ ID NO: 9:

(i) SEQUENCE CHARACTERISTICS:
            (A) LENGTH: 69 base pairs
            (B) TYPE: nucleic acid

```
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 9:

AATATGGTAC CTTTGGATAA AAGAGACTAC AAGGACGACG ATGACAAGAA                  50

CTGGGTGAAT GTAATAAGT                                                   69

(2) INFORMATION FOR SEQ ID NO: 10:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 10:

GCGATATATC CATGGTCAAG AAGTGTTGAT GAACAT                                 36
```